US007014859B1

(12) United States Patent
Duncan et al.

(10) Patent No.: US 7,014,859 B1
(45) Date of Patent: Mar. 21, 2006

(54) ENTOMOPATHOGENIC NEMATODE FOR CONTROL OF INSECT PESTS

(75) Inventors: Larry W. Duncan, Plant City, FL (US); Khuong B. Nguyen, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 497 days.

(21) Appl. No.: 10/197,993

(22) Filed: Jul. 18, 2002

Related U.S. Application Data

(60) Provisional application No. 60/306,313, filed on Jul. 18, 2001.

(51) Int. Cl.
*A01N 63/00* (2006.01)
*A01N 65/00* (2006.01)
*A01N 25/00* (2006.01)
*A01N 25/34* (2006.01)

(52) U.S. Cl. ............... 424/405; 424/93.7; 424/408; 424/451; 424/458; 424/489

(58) Field of Classification Search ............... 424/93.7, 424/405, 408, 451, 458, 489
See application file for complete search history.

(56) References Cited

U.S. PATENT DOCUMENTS 6,184,434 B1 * 2/2001 Raulston et al. ............... 800/8

OTHER PUBLICATIONS

Courtney, Wilbur D. et al., TAF, an Improved Fixative in Nematode Technique, Plant Disease Reporter, Jul. 15, 1955, pp. 570-571, vol. 39, No. 7.
Hominick, W.M. et al., Biosystematics of entomopathogenic nematodes: current status, protocols, and definitions, Journal of Helminthology, 1997, pp. 271-298, vol. 71.1.
Gaugler, Randy, Biological Control Potential of Neoaplectanid Nematodes, Journal of Nematology, Jul. 1981, pp. 241-249, vol. 13, No. 3.
Nguyen, Khuong B. et al., Scanning Electron Microscope Studies of *Steinernema glaseri* (Nematoda: Steinernematidae), Nematologica, 1995, pp. 183-190, vol. 41.
Nguyen, K.B. and G.C. Smart, Jr., *Steinernema scapterisci* n. sp. (Rhabditida: Steinernematidae), Journal of Nematology, 1990, pp. 187-199, vol. 22, No. 2.
Nguyen, Khuong B. and Larry Duncan, *Steinernema diaprepesi* n. sp. (Rhabditida: Steinernematidae), a Parasite of the Citrus Root Weevil *Diaprepes abbreviatus* (L) (Coleoptera: Curculionidae), Journal of Nematology, 2002, pp. 159-170, vol. 34, No. 2.
Poinar, George O. Jr., Taxonomy and Biology of Steinernematidae and Heterorhabditidae, Entomopathogenic Nematodes in Biological Control, 1990, pp. 23-61.

* cited by examiner

*Primary Examiner*—Herbert J. Lilling
(74) *Attorney, Agent, or Firm*—Saliwanchik, Lloyd & Saliwanchik

(57) ABSTRACT

A nematode collected from *Diaprepes abbreviatus* was identified and described as a new species, *Steinernema diaprepesi* n. sp. The new species can be distinguished from other species of the genus by the following characteristics: Males: Spicule averaging 79 (71–90) Fm; the ratio D % (distance from the anterior end/esophagus length×100) about 80; the ratio SW (spicule length/anal body width) about 1.8. Females: Vulva with short, double flapped epiptygma; tail terminus usually with 5 mucrons. Infective juveniles: Body averaging 1002 (880–1133) Fm, EP (distance from anterior end to excretory pore)=74 (66–83) Fm; tail length=83 (65–91) Fm, and E % (EP/tail length)=89.6 78–114). Lateral field pattern variable, the formula for the arrangement of ridges from head to tail is: 2, 6, 7, 8, 4, 2. The portion with 8 ridges is the longest. This new species can be differentiated from the 3 closest species, *S. feltiae, S. glaseri*, and *S. oregonense* by characteristics of their sequences.

13 Claims, 7 Drawing Sheets

```
                          1                                                        50
Steinernema feltiae   GGAAGGATCA TTATTGAGCT TATCCATTTA CTTG---GAT TCAAATGAAT
S. oregonense         GGAAGGATCA TTATTGAGCT TATCCATTTA CTTG---GAT TCAAATGAAT
S. glaseri            GGAAGGATCA TTATTGAGCC TACTCTCATA CATGTGAGTA TTATGATCAC
S. diaprepesi         GGAAGGATCA TTATTGAGCT TA-ACACTTC GTTGTTTATA CGTTACGTAT
                      ********** ********  **   *    *    **                  *

51                                                      100
Steinernema feltiae   CGAGCTGAAT -TTTCGCTGT TCGTTTCAAA GCGTTGTATT CTCTCAACTA
S. oregonense         CGAGCTGAAT CGTTTGCTGT TTGTCTCGAG GCAATGTATT CTCTCATCTA
S. glaseri            TGTTCGGAAC GCGGCACT-G TCGTTTCTAG GTGTCGCGAC CGTTCG-ACA
S. diaprepesi         CGTTCGGAAC GACACTGTCC ACGTTTCTAA GTGTCGATTC CGTTCA-CTA
                       *   * ***          *    ** ** *  *     *    *  **    *

101                                                     150
Steinernema feltiae   ACGGCTATGA ATGGTTTCTA TAGGTGTCTG GAGCAGTTGT ATGAGCGTGA
S. oregonense         ACGGCTATGA ATGGTTTCTA TAGGTGTCTG GAGCAGTTGT ATGAGCGTGA
S. glaseri            ACGGCTTTGA ATGGTTTCTA TAGGTGTCTG GAGCAGCTGT ATGAGCGTGG
S. diaprepesi         ACGGCTTCGA ATGGTTTCTA TAGGTGTCTG GAGCAGCTGT ATGAGCGTGG
                      ******  ** ********** ********** ****** *** ********

151                                                     200
Steinernema feltiae   CTGTGGTGAT GGACATTTTG ---------- ---------- -GTGGCTCCT
S. oregonense         CTGTGGTGAT GGACATTTGA ---------- ---------- -GT-------
S. glaseri            CTGTGGTGAA GGACATTTGA CATCGCGT-- ---------- ----------
S. diaprepesi         CTGTGATGAA GGACATTTAA CATCCTATGC CAGACGTCTA GCTGTCTCTT
                      ***** ***  ********
```

Figure 1(a)

```
                           201                                                    250
Steinernema feltiae        TAGTCGGGTC ACTAGAATTA AAGAAGTCTG TTATGACTCG CCGTTCTT-A
S. oregonense              ---TCTTGTG ACTAGAATTA AAGAAGTCTG ATACGACTCG CCGTTCTTAA
S. glaseri                 -CTCGACGCG GTGAGAATTG AAGAGGTCAG -TCGGAGACC CGCCGTTCAC
S. diaprepesi              GCGTTTGGTG ATGAGAATTA AAGAGGTCAG -TCGGAGACC CGCCGTTCA-
                                    *  ******   ****  ***  *   * **    *    *    *

251                                                    300
Steinernema feltiae        AAAAACTTCA ATTAACGTTT GATCAATTTG ACTGCACCAG CCGT----AG
S. oregonense              AAAAACTTCA ATTAACGTTT GATCAATTTG ACTGCACCAG CCGT----AG
S. glaseri                 AAACCCTACC ATTAACAATT TTACACACGA TGACAAGCAT CGTTGATGCT
S. diaprepesi              AAAACCTACC ATTAACATTT TCCATACTAA GCTCCATATG TATTTATGGT
                           ***   ** * ******  **                        *          *

301                                                    350
Steinernema feltiae        GTGTACTTAA AGATTTATCA AGTCTTGT-C GGTGGATCAC TCGGTTCGTA
S. oregonense              GTGTACTTAA AGATTTATCA AGTCTTGT-C GGTGGATCAC TCGGTTCGTA
S. glaseri                 GTGTTATACA ACTGTTACCA AGTCTTAT-C GGTGGATCAC TCGGTTCGTA
S. diaprepesi              GGCGAAAACA ATGTTATCCA AGTCTTATCC GGTGGATCAC TCGGTTCGTA
                           *            *   *     **  ***** * * ********** **********

351                                                    400
Steinernema feltiae        GTTCGATGAA AAACGGGGCA AAAACCGTTA TTTGGCGTGA ATTGCAGACA
S. oregonense              GTTCGATGAA AAACGGGGCA AAAACCGTTA TTTGGCGTGA ATTGCAGACA
S. glaseri                 GTTCGATGAA AAACGGGGCA AAAACCGTTA TTTGGCGTGA ATTGCAGACA
S. diaprepesi              GTTCGATGAA AAACGGGGCA AAAACCGTTA TTTGGCGTGA ATTGCAGACA
                           ********** ********** ********** ********** **********
```

Figure 1(b)

```
                            401                                              450
Steinernema feltiae   TATTGAACGC TAAAATTTTG AACGCAAATG GCACTATCAG GTTTATATCT
S. oregonense         TATTGAACGC TAAAATTTTG AACGCAAATG GCACTATCAG GTTTATATCT
S. glaseri            TATTGAACGC TAAAATTTTG AACGCAAATG GCACTATCAG GTTTATATCT
S. diaprepesi         TATTGAACGC TAAAATTTTG AACGCAAATG GCACTATCAG GTTAATATCT
                      ********** ********** ********** ********** *** ******

451                                              500
Steinernema feltiae   GTTAGTATGT TTGGTTGAGG GTCGATTAAT TCGTAACCTG CAGTCTGCTG
S. oregonense         GTTAGTATGT TTGGTTGAGG GTCGATTAAT TCGTAACTTG CAGTCTGCTG
S. glaseri            GATAGTATGT TTGGTTGAGG GTCGACTAAC ACGTTACTTG CAGTCAG---
S. diaprepesi         GATAGTATGT TTGGTTGAGG GTCGATTAAC TCGTTACTTG CAGTCAGCTT
                      * ******** **********  ***** ***   *** ** ** ***** *

501                                              550
Steinernema feltiae   TGACTGTTTT TTCGATTAGT TA----TTTG GTTTTTTTAT CGAGTACCTT
S. oregonense         TGACTGTTTT TCCGATTAGT TACTCGATTG GCTCGCTGAT CGAGTACCTT
S. glaseri            CGACTGTTTT TTCGACGAGC TATCTAC--G TTCGTATGTA CCTCGTTCGG
S. diaprepesi         CGACTGTTTA TTCGATAAGC TACTTCGAG CTGCGAAAGT ACCTTTTCGG
                      ********    * *** **  **    *              *

551                                              600
Steinernema feltiae   TTTGGAATGT GAA-TTTGAT TGTCTAATTC GTTTCCTAAT CGAA---ACG
S. oregonense         CTAGGTATGT GAATTTTGAT AGTCTAATTC GTTTCCTAAT CGAA---ACT
S. glaseri            TGTGAACGTT CCCCCGGCAC TGGGGGCGAT ACTGCAATGG ACAAGGCTTT
S. diaprepesi         TGTGAACGCT TCAATGCGAT AGGCTAATGG AGGTCGTTAG GCGAGTGTCT
                          *    *        *      *   *       *                *
```

Figure 1(c)

```
                     601                                                        650
Steinernema feltiae  AGCTATTTTT TATTTCT-GT GCAATGTATT TTTGGTGTTT CGGCGTTTTT
S. oregonense        AGCTATCTTT GAATTCTGgT GCGTTGTATC TTTGGTGTTT CGGCGCGTTT
S. glaseri           -------TGT CGTGTCCGCT ATCACATCGG TTCCGTGCGT T-GATGGCTT
S. diaprepesi        CTTTCGCTAA CGCTTCTGCT ATCATATCGG TTCTGTGCGT TACGTGGCTA
                              *      **   *       *     ** ***  *            *

651                                                        700
Steinernema feltiae  CTTGCCGACT GATTGGTACA AACTTAACAG TTCGTATATT TTTCAGAATT
S. oregonense        CTTGCCGACT GATCTGTACG TA-------- ACCGTATATG CTTCA-ATTT
S. glaseri           TGGCGTGTCT CTTGCCAGCT GACTTGTACG TAATTTTTTG CGTATGTAAG
S. diaprepesi        TGGCGTGTCT CTTGCCAGTT GACTTGTACG CAGACGTAAC TGTCTCGTAT
                      *  **          *           *              *           *

701                                                        750
Steinernema feltiae  TTTCAGAGGC CCTTACAATA CATCACTTGA CACAACACGT ATCGTTTGTC
S. oregonense        GATCAGATGC CCTTAGCTTA CTTCACTCGA CACAACACGT TTCGTTTGTT
S. glaseri           CTTCTTGAAG TCAGTGTTGC CAGCAAGCGT TTGAGCCTGT ACGGTTCGGC
S. diaprepesi        GTAAGCTTCT TCA-AGTCGG CTGCCACATG TTCGACCTTT GCGGGTTGAC
                              *         *                      *   *    * * *

751                                                        800
Steinernema feltiae  GAGGAATTGC GCAAGAA--- -----AGAAA CTTTTCGTTT TACGACCTCA
S. oregonense        GAGTAATCGC GCAAAAa--- -TTGTAAACT TTTtCGTTTT tACGACCTCA
S. glaseri           GCGCGACGTA GCTGGGACTT CGTGTTCGAT GTTTTCGAAT GACGACCTCA
S. diaprepesi        GAACGCAACT GGAACTTGCT CG-ATTCGAT GTTTTCGAAT TACGACCTCA
                       *          *                      ***    *  ********
```

Figure 1(d)

```
                           801         814
Steinernema feltiae    ACTCAAGCAA  GATT
S. oregonense          ACTCAAGCAA  GACT
S. glaseri             ACTCAAGCAA  GACT
S. diaprepesi          ACTCAAGCAA  GACT
                       **********  ** *
```

\* no differences found among nematode species.

Figure 1(e)

SEQUENCE LISTING

<160> NUMBER OF SEQ ID NOS: 8

<210> SEQ ID NO 1
<211> LENGTH: 21
<212> TYPE: DNA
<213> ORGANISM: Steinernema diaprepesi

<400> SEQUENCE: 1
atatgcttaa gttcagcggg t     21

```
<210> SEQ ID NO 2
<211> LENGTH: 20
<212> TYPE: DNA
<213> ORGANISM: Steinernema diaprepesi

<400> SEQUENCE: 2
gtttccgtag gtgaacctgc                                              20

<210> SEQ ID NO 3
<211> LENGTH: 19
<212> TYPE: DNA
<213> ORGANISM: Steinernema diaprepesi

<400> SEQUENCE: 3
gtatgtttgg ttgaaggtc                                               19

<210> SEQ ID NO 4
<211> LENGTH: 19
<212> TYPE: DNA
<213> ORGANISM: Steinernema diaprepesi

<400> SEQUENCE: 4
cacgctcata caactgctc                                               19

<210> SEQ ID NO 5
<211> LENGTH: 814
<212> TYPE: DNA
<213> ORGANISM: Steinernema feltiae
<220> FEATURE:
<221> NAME/KEY: misc_feature
<222> LOCATION: ()..()
<223> OTHER INFORMATION: n is an unknown nucleotide defined as a, t, g,
      or c.

<400> SEQUENCE: 5
ggaaggatca ttattgagct tatccattta cttgnnngat tcaaatgaat cgagctgaat   60
ntttcgctgt tcgtttcaaa gcgttgtatt ctctcaacta acggctatga atggtttcta  120
taggtgtctg gagcagttgt atgagcgtga ctgtggtgat ggacattttg nnnnnnnnnn  180
nnnnnnnnnn ngtggctcct tagtcgggtc actagaatta agaagtctg ttatgactcg   240 ccgttcttna aaaacttca attaacgttt gatcaatttg actgcaccag ccgtnnnnag   300
gtgtacttaa agatttatca agtcttgtnc ggtggatcac tcggttcgta gttcgatgaa  360
aaacggggca aaaccgtta tttggcgtga attgcagaca tattgaacgc taaaattttg   420
aacgcaaatg gcactatcag gtttatatct gttagtatgt ttggttgagg gtcgattaat   480
tcgtaacctg cagtctgctg tgactgtttt ttcgattagt tannnntttg gttttttat   540 cgagtacctt tttggaatgt gaantttgat tgtctaattc gtttcctaat cgaannnacg  600
agctattttt tatttctngt gcaatgtatt tttggtgttt cggcgttttt cttgccgact  660
gattggtaca aacttaacag ttcgtatatt tttcagaatt tttcagaggc ccttacaata  720
catcacttga cacaacacgt atcgtttgtc gaggaattgc gcaagaannn nnnnnagaaa  780
cttttcgttt tacgacctca actcaagcaa gatt                             814

<210> SEQ ID NO 6
<211> LENGTH: 814
<212> TYPE: DNA
<213> ORGANISM: Steinernema oregonense
```

<220> FEATURE:
<221> NAME/KEY: misc_feature
<222> LOCATION: ()..()
<223> OTHER INFORMATION: n is an unknown nucleotide defined as a, t, g, or c.

<400> SEQUENCE: 6

| | | | | | |
|---|---|---|---|---|---|
| ggaaggatca | ttattgagct | tatccattta | cttgnnngat | tcaaatgaat | cgagctgaat | 60 |
| cgtttgctgt | ttgtctcgag | gcaatgtatt | ctctcatcta | acggctatga | atggtttcta | 120 |
| taggtgtctg | gagcagttgt | atgagcgtga | ctgtggtgat | ggacatttga | nnnnnnnnnn | 180 |
| nnnnnnnnnn | ngtnnnnnnn | nnntcttgtg | actagaatta | agaagtctg | atacgactcg | 240 |
| ccgttcttaa | aaaaacttca | attaacgttt | gatcaatttg | actgcaccag | ccgtnnnnag | 300 |
| gtgtacttaa | agatttatca | agtcttgtnc | ggtggatcac | tcggttcgta | gttcgatgaa | 360 |
| aaacggggca | aaaaccgtta | tttggcgtga | attgcagaca | tattgaacgc | taaaattttg | 420 |
| aacgcaaatg | gcactatcag | gtttatatct | gttagtatgt | ttggttgagg | gtcgattaat | 480 |
| tcgtaacttg | cagtctgctg | tgactgtttt | tccgattagt | tactcgattg | gctcgctgat | 540 |
| cgagtacctt | ctaggtatgt | gaattttgat | agtctaattc | gtttcctaat | cgaannnacg | 600 |
| agctatcttt | gaattctggt | gcgttgtatc | tttggtgttt | cggcgcgttt | cttgccgact | 660 |
| gatctgtacg | tannnnnnnn | accgtatatg | cttcanattt | gatcagatgc | ccttagctta | 720 |
| cttcactcga | cacaacacgt | ttcgtttgtt | gagtaatcgc | gcaaaaannn | nttgtaaact | 780 |
| ttttcgtttt | tacgacctca | actcaagcaa | gact | | | 814 |

<210> SEQ ID NO 7
<211> LENGTH: 814
<212> TYPE: DNA
<213> ORGANISM: Steinernema glaseri
<220> FEATURE:
<221> NAME/KEY: misc_feature
<222> LOCATION: ()..()
<223> OTHER INFORMATION: n is an unknown nucleotide defined as a, t, g, or c.

<400> SEQUENCE: 7

| | | | | | |
|---|---|---|---|---|---|
| ggaaggatca | ttattgagcc | tactctcata | catgtgagta | ttatgatcac | tgttcggaac | 60 |
| gcggcactng | tcgtttctag | gtgtcgcgac | cgttcgnaca | acggctttga | atggtttcta | 120 |
| taggtgtctg | gagcagctgt | atgagcgtgg | ctgtggtgaa | ggacatttga | catcgcgtnn | 180 |
| nnnnnnnnnn | nnnnnnnnnn | nctcgacgcg | gtgagaattg | aagaggtcag | ntcggagacc | 240 |
| cgccgttcac | aaaccctacc | attaacaatt | ttacacacga | tgacaagcat | cgttgatgct | 300 |
| gtgttataca | actgttacca | agtcttatnc | ggtggatcac | tcggttcgta | gttcgatgaa | 360 |
| aaacggggca | aaaaccgtta | tttggcgtga | attgcagaca | tattgaacgc | taaaattttg | 420 |
| aacgcaaatg | gcactatcag | gtttatatct | gatagtatgt | ttggttgagg | gtcgactaac | 480 |
| acgttacttg | cagtcagnnn | cgactgtttt | ttcgacgagc | tatgtacnng | ttcgtatgta | 540 |
| cctcgttcgg | tgtgaacgtt | cccccggcac | tgggggcgat | agtgcaatgg | acaaggcttt | 600 |
| nnnnnnntgt | cgtgtccgct | atcacatcgg | ttccgtgcgt | tngatggctt | tggcgtgtct | 660 |
| cttgccagct | gacttgtacg | taatttttg | cgtatgtaag | cttcttgaag | tcagtgttgc | 720 |
| cagcaagcgt | ttgagcctgt | acggttcggc | gcgcgacgta | gctgggactt | cgtgttcgat | 780 |
| gttttcgaat | gacgacctca | actcaagcaa | gact | | | 814 |

```
<210> SEQ ID NO 8
<211> LENGTH: 814
<212> TYPE: DNA
<213> ORGANISM: Steinernema diaprepesi
<220> FEATURE:
<221> NAME/KEY: misc_feature
<222> LOCATION: ()..()
<223> OTHER INFORMATION: n is an unknown nucleotide defined as a, t, g,
      or c.

<400> SEQUENCE: 8
ggaaggatca ttattgagct tanacacttc gttgtttata cgttacgtat cgttcggaac      60
gacactgtcc acgtttctaa gtgtcgattc cgttcancta acggcttcga atggtttcta     120
taggtgtctg gagcagctgt atgagcgtgg ctgtgatgaa ggacatttaa catcctatgc     180
cagacgtcta gctgtctctt gcgtttggtg atgagaatta aagaggtcag ntcggagacc     240
cgccgttcan aaaacctacc attaacattt tccatactaa gctccatatg tatttatggt     300
ggcgaaaaca atgttatcca agtcttatcc ggtggatcac tcggttcgta gttcgatgaa     360
aaacggggca aaaaccgtta tttggcgtga attgcagaca tattgaacgc taaaattttg     420
aacgcaaatg gcactatcag gttaatatct gatagtatgt ttggttgagg gtcgattaac     480
tcgttacttg cagtcagctt cgactgttta ttcgataagc tactttcgag ctgcgaaagt     540 acctttcgg tgtgaacgct tcaatgcgat aggctaatgg aggtcgttag gcgagtgtct     600 cttcgctaa cgcttctgct atcatatcgg ttctgtgcgt tacgtggcta tggcgtgtct     660
cttgccagtt gacttgtacg cagacgtaac tgtctcgtat gtaagcttct tganagtcgg     720
ctgccacatg ttcgaccttt gcgggttgac gaacgcaact ggaacttgct cgnattcgat     780
gttttcgaat tacgacctca actcaagcaa gact                                 814
```

ENTOMOPATHOGENIC NEMATODE FOR CONTROL OF INSECT PESTS

This application claims the benefit of 60/306,313, filed Jul. 18, 2001.

FIELD OF THE INVENTION

Citrus root weevils, including *Diaprepes abbreviatus* (L) and several other species of curculionid insects, are prominent pests of citrus crops throughout Florida and the Caribbean. This invention relates to a novel entomopathogenic nematode of the genus *Steinernema*, which is effective as a biopesticide for the control of insects, and particularly citrus root weevils.

BACKGROUND OF THE INVENTION

Several insect species in the family Curculionidae are commonly referred to as citrus root weevils. In Florida, and throughout the Caribbean region, the West Indian sugarcane borer weevil, *Diaprepes abbreviatus* L., is the root weevil of greatest economic significance to citrus. The insect was first detected in Florida in 1964, and currently infests an estimated 150,000 of the 845,000 acres of commercial citrus orchards. During the past decade, *D. abbreviatus* has become the most serious biological threat to the well-being of citriculture in Florida because of its high incidence, its devastating effect on trees, and because cost-effective IPM strategies have been elusive. Prior to 1998, attempts to intervene in the soil-borne phase of the weevil life cycle were hampered by the absence of registered, effective soil-applied pesticides, due to environment concerns. For these reasons, the use of entomopathogenic nematodes to manage citrus root weevils has had a high priority for more than a decade among both researchers and citrus growers in Florida. Adult *D. abbreviatus* feed and oviposit on the leaves of citrus and alternate host plants in orchards. Newly-hatched (neonate) larvae drop to the soil where they develop for 4–9 months while feeding on the root systems of trees. Pupation occurs in the soil. Young larvae feed initially on the small fibrous roots but as they increase in size they feed on the cortex of more mature, larger roots. The insects create long lesions or channels in the bark of the larger roots, which are then infected by the root-rotting fungi *Phytophthora nicotianae* Dastur, and *P. palmivora* (Butler) Butler (McCoy, 1999: Graham & Menge, 1999). The interaction between root weevils and plant pathogenic fungi results in one of the most severe decline syndromes affecting citrus. Trees are sometimes killed by resulting crown rot, but more typically, trees decline rapidly and irreversibly due to cambium girdling and death of large structural roots.

Entomopathogenic nematodes are widely used by Florida citrus growers as an Insect Pest Management tactic for control of citrus root weevils (*Diaprepes abbreviatus*). Nematodes of the genera *Steinernema* and *Heterorhabditis* possess most of the characteristics of an ideal biological control agent for insects [Poiner, Taxonomy and Biology of Steinemematidae and Heterorhabditidae, In Gaugler and Kaya (eds.), Entomopathogenic Nematodes in Biological Control, CRC Press, Boca Raton, Fla., (1990), pages 23–61; and Gaugler, J. Nematol., 13:241–249, (1981)]]. These nematodes search for their insect hosts; they are highly virulent, killing most hosts within 48 hours; they are easily and inexpensively mass produced; they can be conveniently applied in irrigation water; and they have a wide range of insect hosts (Poiner, ibid and Gaugler, ibid). Moreover, the nematodes are a form of biological control, and therefore present fewer issues than do chemical pesticides concerning safety and environmental degradation. The effectiveness of these nematodes is attributed to a mutualistic bacterium of the genus *Xenorhabdus* associated therewith [Poiner, ibid]. After entry or penetration of the nematode into the insect host, the bacteria are released from the nematode and rapidly multiply, killing the host insect by septicemia. Conversely, the nematodes protect the bacteria from the environment prior to release within a suitable host. However, management of citrus root weevils with nematodes or with chemical measure is relatively inefficient, given the severe level of damage to citrus caused by the weevils. Therefore, improved efficacy of nematodes by virtue of greater virulence or persistence in the soil is desirable. Disclosed herein is a new nematode, which has a demonstrated ability to persist in soil in Florida citrus groves. The virulence of the new nematode in bioassays is superior to that of commercially available nematode species.

All documents cited herein are incorporated by reference in their entirety, to the extent not inconsistent with the explicit teachings set forth herein.

BRIEF SUMMARY OF THE INVENTION

We have now discovered a previously unknown entomopathogenic nematode of the genus *Steinernema*, which is effective as a biopesticide for the control of insects, and particularly citrus root weevils. This nematode has been identified as *Steinernema diaprepesi* (a deposit of which was made on Mar. 30, 2005, under the terms of the Budapest Treaty, at American Type Culture Collection, 10801 University Blvd., Manassas, Va. 20110–2209 and assigned accession No. PTA-6654.

A nematode was collected from larvae of *Diaprepes abbreviatus* (L) buried in cages beneath citrus trees in Polk County, Florida. While the nematode is a member of the genus *Steinernema*, it is different morphologically from other species of the genus. The nematode has some characteristics of *S. feltiae*, *S. glaseri*, and *S. oregonense*, but is distinguishable. Molecular techniques and cross hybridization were used to evaluate the relationship between the new species and these three nematodes. The studies proved that the nematode is a new species. The new species is described herein as *Steinernema diaprepesi* n. sp. named after the host insect from which the nematode was collected.

To provide a better understanding of a number of terms used in this specification and claims herein, the following definitions are provided:

The term "substantially biologically pure inert carrier" as used herein, is defined as an inert carrier having significantly fewer naturally occurring microorganisms relative to the environment.

An "insecticidally effective amount" as used herein, is defined as that quantity of nematode which will result in a mortality rate of a test group of insects greater than 50% compared to an untreated group of the same insects.

The nematode of this invention has been isolated in pure form from the larvae of *Diaprepes abbreviatus* (L) that were buried in cages beneath citrus trees in Polk County, Florida. A *S. diaprepesi* was discovered parasitizing >50% of caged, buried *D. abbreviatus* larvae in experimental plots in a citrus orchard that were established to evaluate management tactics against the weevil. The nematode is related to *Steinernema feltiae*, *S. glaseri*, and *S. oregonense*, but differs from these species based on morphology, cross hybridization, and composition of the internal transcribed spacer regions (ITS1 and ITS2) of rDNA. The efficacy of the new nematode against *D. abbreviatus* was compared in the laboratory to *Steinernema riobrave*, which is a commercially available species utilized to manage insects. In Petri dishes containing moist sand, *S. diaprepesi* killed *D. abbreviatus* at a higher rate than *S. riobrave*. Cumulative mortality for both species exceeded 90% over a period of 30 days. *Steinernema diaprepesi* exited insect cadavers (recycled) sooner than *S. riobrave*. It is a larger nematode and produces about 35% fewer offspring than *S. riobrave*. *Steinernema diaprepesi* moved 20 cm through sand columns in 4 days to kill 70% of buried larvae of *D. abbreviatus* compared to 15% for *S. riobrave*. *D. abbreviatus* cadavers infected by either nematode were maintained in Petri dishes containing moist sand at 22–25° C. to evaluate the relative persistence in soil of the two species. Live insect larvae were periodically added to the dishes. Both species killed >90% of the newly introduced insects for up to 90 days, however, *S. diaprepesi* recycled in the freshly killed insects at a significantly higher rate. *S. diaprepesi* killed 100% of newly introduced insects after 210 days in the dishes, compared to 60% for *S. riobrave*. Recycling of *S. riobrave* and *S. diaprepesi* after 210 days in sand was 10% and 90%, respectively. When applied to the locus of the target insects, *S. diaprepesi* provides improved suppression of the insect population.

In accordance with this discovery, it is an object of this invention to introduce Steinernema diaprepesi as a novel biopesticide for the control of insects. Further objects and advantages will become apparent by reference to the following detailed description of the invention and appended figures.

BRIEF DESCRIPTION OF THE DRAWINGS

FIGS. 1(a) through (e) are a comparison of polynucleotide sequence homology among *Steinernema feltiae*, *S. oregonense*, *S. glaseri*, and *S. diaprepesi*.

BRIEF DESCRIPTION OF THE SEQUENCES

Figure 2A:
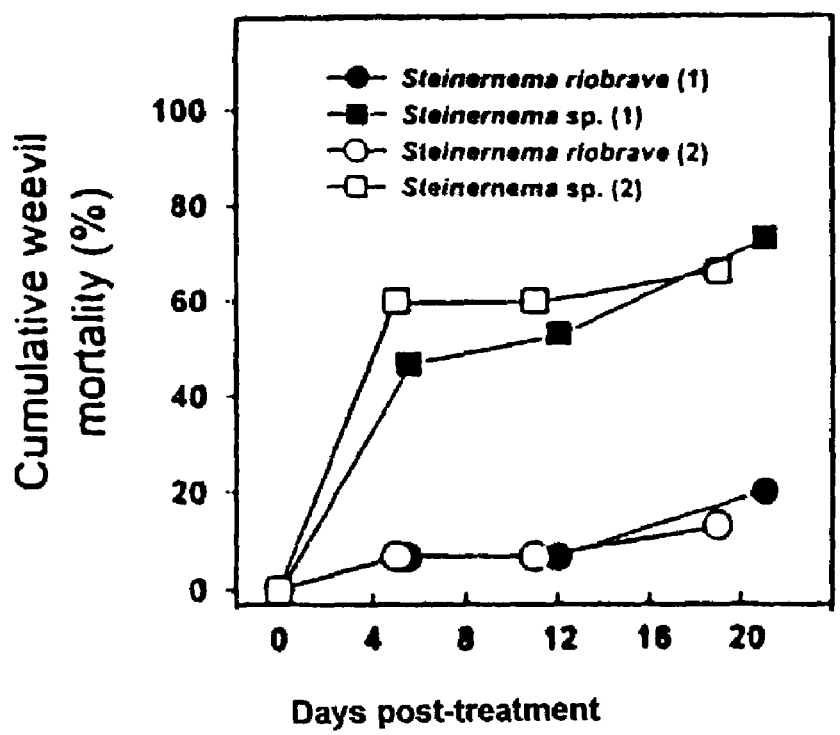
FIG. 2(a) is a graphical comparison of the effect of *S. riobrave* and *S. diaprepesi* on citrus root weevil larvae mortality.

SEQ ID NO:1 is the polynucleotide sequence for primer AB28.

SEQ ID NO:2 is the polynucleotide sequence for primer TW81.

SEQ ID NO:3 is the polynucleotide sequence for primer KN58.

SEQ ID NO:4 is the polynucleotide sequence for primer KNRV.

SEQ ID NO:5 is a polynucleotide sequence from *Steinernema feltiae*.

SEQ ID NO:6 is a polynucleotide sequence from *Steinernema oregonense*.

SEQ ID NO:7 is a polynucleotide sequence from *Steinernema glaseri*.

SEQ ID NO: 8 is a polynucleotide sequence from *Steinernema diaprepesi*.

DETAILED DISCLOSURE OF THE INVENTION

Nematode Extraction and Characterization

*Steinernema diaprepesi* n.sp. was isolated from larvae of *Diaprepes abbreviatus* that were buried in cages beneath citrus trees as part of an experiment to evaluate the insecticidal efficacy of commercially available entomopathogenic nematodes. During 2 years of the experiment, indigenous populations of *S. diaprepesi* infected and killed 13–50% of the buried insects within seven days, with higher rates of parasitism during the summer compared to spring and autumn months. The nematode was isolated with much lower frequency from the rhizosphere of native plants growing between tree rows than from the rhizosphere of citrus trees.

The topotype locality is an irrigated, commercial citrus orchard c. 3 k east of Bartow, and immediately southeast of the intersection of Cowpen Road and 80-Foot Road. Mean monthly temperatures range from 16.1–27.9° C. and cumulative annual precipitation averages 1364 mm with most rainfall occurring May–September and frequent periods of drought from mid-autumn to late-spring. Soil texture is astatula sand having a ratio of 97:1:2, (sand:silt:clay, respectively). *Steinernema diaprepesi* has been isolated from other orchards located on the central ridge of Florida characterized by deep sandy soils. Attempts to isolate the nematode in heavier-textured soils off of the central ridge have been unsuccessful; however, no comprehensive survey has yet been conducted.

Host and Locality:

The nematode was collected from an infested citrus root weevil *Diaprepes abbreviatus* (L), in a commercial citrus orchard, Polk County, Florida.

Type Specimens

Holotype (male, first generation): A first generation male was isolated from the hemocoel of a *Galleria mellonella*, and deposited in the United States Department of Agriculture Nematode Collection (USDANC), Beltsville, Md.

Allotype (female, first generation): A first generation female was isolated from the hemocoel of *Galleria mellonella* and deposited in the USDANC, Beltsville, Md.

Paratypes (first-generation males and females, and third-stage infective juveniles): Same data as holotype. Many males and females of the first generation and several third-stage infective juveniles in TAF, in a vial, deposited in USDANC Beltsville, Md. Several males, and females of the first generation, and several third stage infective juveniles deposited in the Florida Collection of Nematodes, Florida Department of Agriculture and Consumer Service, Gainesville, Fla. One male and one female of the first generation, and several infective juveniles deposited in the California Collection of Nematodes, University of California Davis Nematode Collection, Davis, Calif.

Diagnosis. Males: Males have a spicule averaging about 79 (71–90) Fm and a D % about 80. The SW ratio is about 1.8 and has a lateral field with one narrow ridge. Females have a vulva with a short, double flapped epiptygma. The tail terminus usually has 5 mucrons. Infective juveniles have a body averaging about 1002 (880–1133) Fm, EP=74 (66–83) Fm tail length=83 (65–91) Fm, and E %=89.6 78–114). The lateral field pattern is variable, the number of ridges in each portion from head to tail is: 2, 6, 7, 8, 4, 2. The portion with 8 ridges is the longest.

Relationship: *Steinernema diaprepesi* n. sp. can be distinguished from other *Steinernema* species by the characteristics of males, females, and infective juveniles. Males can be differentiated from other nematodes by shape, length of spicules and gubernaculum, number of genital papillae (25 in this species vs. 23 for others), the presence of one narrow ridge in the lateral field, D %=80, and SW=1.8. Females can be distinguished from other species by the presence of 5 mucrons on the tail tip, and vulva with typical epiptygma. Infective juveniles of the new species can be recognized by body length (1002 Fm), distance from anterior end to excretory pore, tail length, and E %. The pattern of the lateral field of this nematode differs compared to the patterns of other species. Finally, *Steinernema diaprepesi* n. sp. can be differentiated from the 3 closest species (*S. feltiae, S. oregonense, S. glaseri*) by sequence analysis as described herein and illustrated in FIG. 1(*a*) through (*e*).

pronounced sclerotized structure at the anterior end. There is an excretory pore near nerve ring, usually located just anterior to the basal bulb. The esophagus is cylindrical anteriorly, the metacorpus slightly swollen, there is an isthmus present, and the basal bulb is distinct with a nerve ring around the anterior end. The esophago-intestinal valve is distinct. The gonad is monarchic and reflexed. The distance from the base of the esophagus to the anterior end of the testis is variable. Spicules are paired and brown in color. The head (manubrium) of spicules is elongated, in some it is twice as long as it is wide. The shaft (calomus) is very short or absent. The blade (lamina) is thick, tapering slightly posteriorly, with a terminus that is blunt with a longitudinal depression slit in the ventral side. The velum is present. Each spicule has 2 internal ribs. The gubernaculum is boat-shaped; the anterior part usually has one or two ventral projections. These are eleven pairs (occasionally twelve) and one single precloacal genital papillae. The tail conoid, and the tail terminus are without mucron.

TABLE 1

Measurements (in μm) of male *Steinernema diaprepesi* n. sp.
Collected from *Galleria mellonella* and *Diaprepes abbreviatus*. (n = 20)

| | Reared using *Galleria* (First generation) | | | Reared using *Diaprepes* (First generation) | | | Reared using *Galleria* (Second generation) | | |
|---|---|---|---|---|---|---|---|---|---|
| Charactera | Means | SD | Range | Means | SD | Range | Means | SD | Range |
| Body length | 1735 | 156 | 1506–2078 | 1403 | 185 | 1060–1693 | 1176 | 117 | 1036–1343 |
| Greatest width | 113 | 15 | 90–145 | 78 | 11 | 61–100 | 64 | 7 | 54–78 |
| EP | 115 | 9 | 100–130 | 100 | 13 | 74–117 | 83 | 8 | 71–108 |
| NR | 119 | 6 | 109–129 | 121 | 11 | 100–139 | 110 | 8 | 100–136 |
| ES | 150 | 7 | 136–162 | 148 | 11 | 127–168 | 138 | 12 | 129–168 |
| Testis reflexion | 391 | 68 | 241–542 | 289 | 51 | 211–380 | 264 | 16 | 187–428 |
| T | 25 | 3 | 20–32 | 25 | 3.2 | 21–32 | 24 | 5 | 18–30 |
| ABW | 42 | 11 | 36–50 | 40 | 4 | 30–45 | 34 | 6 | 29–42 |
| Spicule length | 79 | 5 | 71–90 | 66 | 5 | 57–76 | 69 | 8 | 61–76 |
| Spicule width | 16 | 2 | 14–20 | 12.3 | 1.7 | 9–15 | 12.5 | 3 | 11–15 |
| Gub. length | 54 | 5 | 45–61 | 44 | 3.8 | 38–53 | 40 | 6 | 30–53 |
| Gub. width | 8.7 | 1.4 | 6–12 | 6.7 | 1.3 | 4.6–9.1 | 67 | 1.4 | 5–9 |
| D = EP/ES (%) | 80 | 6 | 68–86 | 68 | 8 | 52–80 | 60 | 8 | 54–67 |
| SW | 1.8 | 1.3 | 1.5–2.0 | 1.7 | 0.3 | 1.2–2.1 | 2 | 0.2 | 1.66–2.33 |
| GS | 0.69 | 0.1 | 59–79 | 0.66 | 0.04 | 0.62–0.74 | 0.59 | 0.07 | 0.46–0.73 |

SD = standard deviation;
EP = distance from anterior end to excretory pore;
NR = distance from anterior end to nerve ring;
ES = distance from anterior end to end of esophagus;
T = tail length;
ABW = anal body width.
a = body length/greatest width;
b = body length/ES;
c = body length/T;
Gub = gubernaculum;
SW = spicule length/ABW;
GS = gubernaculum length/spicule length.

Characterization

*Steinernema diaprepesi* n. sp. has the following characteristics:

Holotype, Males, first generation: Measurements of 20 males are illustrated in Table 1. The body is curved posteriorly and becomes C-shaped when the organism is heat-killed. The lateral field is present in the mid-body with one narrow ridge. The head is rounded and usually slightly swollen. The anterior end has a ring around stoma, 6 labial papillae, 2 amphids (usually covered with exudate), and 4 cephalic papillae. The stoma is shallow, usually with a Morphological characteristics of males collected from *Diaprepes* are similar to those collected from *Galleria*; however, the morphometrics are different (Table 1). Most measurements of males from *Diaprepes* are shorter than those collected from *Galleria*. This indicates that, when possible, *Steinernema* species should be reared in *Galleria* for nematode description or identification.

Males, second generation: Measurements of 10 males are given in Table 1. The second-generation male is similar to that of the first generation except that it is smaller, thinner, the excretory pore much more anterior, and the isthmus more distinct. In addition, the spicules and gubernaculums are shorter and thinner than those of first generation males (Table 1), as well as the occasional presence of a mucron on the tail terminus.

Females, first generation: Measurements of 10 females is illustrated in Table 2. The body cuticle is either smooth or has faint annules. Lateral fields and phasmids are absent. The head is rounded, continuous with body; 6 labial papillae, 4 cephalic papillae. Lips are indistinct. Amphids are present. The stoma is shallow, subtriangle anteriorly and triradiate internally. Cheilorhabdions are prominent and well sclerotized. Another smaller sclerotized structure is located posterior to cheilorhabdions, presumably the prorhabdions. The esophagus has procorpus, is cylindrical and muscular. The metacorpus is swollen. The isthmus is distinct. The basal bulb is enlarged and valvate. A nerve ring surrounds isthmus, just anterior to basal bulb. The esophago-intestinal valve is prominent. There is an excretory pore located right anterior to basal bulb. The gonads are amphidelphic, reflexed, and often contain many eggs. The vulva is a protruding transverse slit and a small double-flapped epiptygma is present. The vagina sclerotized, short, and posteriorly directed in mature females. The body width is greater anterior to vulva than posterior to vulva. The tail shape is variable. Ventral postanal swelling is present. The tail is shorter than the anal body width. Most females have five mucrons on the tail tip that are prominent under a light microscope. These mucrons are variable in length, depending on obesity, and longer with young females.

protruding; however, the epiptygma is usually more prominent. The tail, which tapers to a point, is longer than anal body width. Ventral, postanal swelling is present.

Infective juveniles: The measurements of 50 juveniles are illustrated in Table (3). The body is elongate and the sheath (second-stage cuticle) is generally present, but sometimes lost. The labial region is smooth, continuous, and rounded anteriorly. The labial papillae are not seen; however, 4 cephalic papillae are prominent. Amphids are present but not prominent. The cuticle is marked with a prominent transverse annulation. The lateral field begins anteriorly with a single line. Two additional lines appear at annules 14 and 16 to form 2 ridges. The number of ridges in lateral fields near the excretory pore increases from 2 to 6. About a body width posterior to excretory pore, an additional central ridge appears, making a total of 7 in the lateral field. Near the end of esophagus, the central ridge divides into 2 parts, making a total of 8, the maximum number in the lateral field. The portion with 8 ridges is the longest part of the lateral field. At the level of the anus, the two marginal and two central ridges disappear, only four ridges remain in the lateral field. At about mid-tail the 4 ridges in the lateral field become 2 ridges. Near the tail terminus, the two marginal lines in the lateral field converge, and the central line disappears before reaching the end of the lateral field. The esophagus has a thin anterior part and the basal bulb is elongated with a visible valve. The tail is attenuate and tapers gradually. The hyaline portion of the tail occupies about 57% (50–63) of the total length.

The morphometrics of infective juveniles reared from *Galleria* and from *Diaprepes* are different (Table 3). Conse-

TABLE 2

Measurements (in $\mu$m) of female *Steinernema diaprepesi* n. sp. Collected from *Galleria mellonella* (n = 10)

| Charactera | First generation | | | Second generation | | |
|---|---|---|---|---|---|---|
| | Means | SD | Range | Means | SD | Range |
| Body length | 6512 | 1109 | 5091–7788 | 2385 | 49 | 2030–2697 |
| Stoma length | 9.8 | 3.1 | 7.6–13.6 | — | — | — |
| Stoma width | 10.7 | 3.2 | 9–12 | — | — | — |
| Greatest width | 264 | 29 | 222–307 | 149 | 12 | 137–167 |
| EP | 174 | 41 | 104–214 | 122 | 11 | 111–132 |
| NR | 138 | 34 | 112–165 | 145 | 12 | 132–153 |
| ES | 193 | 27 | 119–211 | 179 | 13 | 167–195 |
| T | 48 | 7 | 38–61 | 75 | 9 | 67–82 |
| ABW | 84 | 9 | 72–96 | 46 | 7 | 39–51 |
| V % | 51 | 7 | 48–57 | 54 | 7 | 49–60 |
| D = EP/ES (%) | 96 | 5 | 91–105 | 68 | 4 | 62–74 |

SD = standard deviation;
EP = distance from anterior end to excretory pore;
NR = distance from anterior end to nerve ring;
ES = distance from anterior end to end of esophagus;
T = tail length;
ABW = anal body width,
a = body length/greatest width;
b = body length/ES;
c = body length/T;
— = not collected.

Females, second generation: The measurements of 20 females are also illustrated in Table 2. The second generation is similar to the first generation female, but smaller (length=2385 $\mu$m, width=149 $\mu$m compared to 6512 $\mu$m and 264 $\mu$m, for first-generation female). The vulva is less quently, choosing an insect host to work for a new species description or identification is important as discussed above for the first generation males.

Cross hybridization test: The test gave negative results except for males and females of the same species.

TABLE 3

Measurements (in μm) of infective juveniles of Steinernema diaprepesi n. sp. collected from Galleria mellonella and Diaprepes abbreviatus (n = 50).

| Charactera | Reared using Galleria | | | Reared using Diaprepes | | |
|---|---|---|---|---|---|---|
| | Means | SD | Range | Means | SD | Range |
| Body length | 1002 | 53 | 880–1133 | 957 | 31 | 807–1030 |
| Greatest width | 34 | 3.6 | 30–42 | 36 | 6 | 29–42 |
| EP | 74 | 6.4 | 66–83 | 69 | 8 | 55–77 |
| NR | 102 | 6 | 74–109 | — | — | — |
| ES | 138 | 7.4 | 111–152 | — | — | — |
| T | 83 | 5 | 65–91 | 81 | 9 | 76–88 |
| ABW | 23 | 2.3 | 21–27 | — | — | — |
| a | 30 | 2.6 | 23–35 | 26.5 | 1.6 | 23–29 |
| b | 7.3 | 0.5 | 6.5–8.3 | — | — | — |
| c | 12.1 | 0.7 | 10.4–13.2 | 11.7 | 0.7 | 10–13 |
| D = EP/ES (%) | 54 | 5 | 30–70 | — | — | — |
| E = EP/T (%) | 90 | 6.5 | 78–114 | 85 | 9 | 71–96 |

SD = standard deviation;
EP = distance from anterior end to excretory pore;
NR = distance from anterior end to nerve ring;
ES = distance from anterior end to end of esophagus;
T = tail length;
ABW = anal body width,
a = body length/greatest width;
b = body length/ES;
c = body length/T;
— = not collected.

Figure 2B:
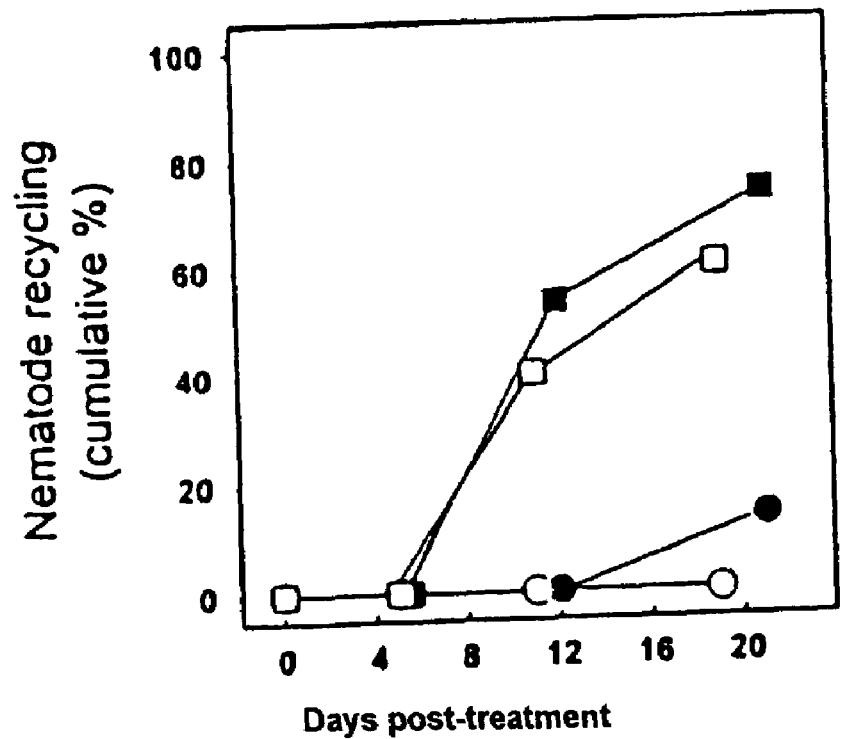
FIG. 2(b) is a graphical depiction of the comparison of recycling rates of *S. riobrave* and *S. diaprepesi*.

Referring now to FIGS. 2a and 2b, and figures graphically depict the efficacy of Steinernema riobrave and the newly discovered Steinernema diaprepesi against citrus root weevil larvae in two laboratory experiments. Nematodes were required to migrate a distance of 15 cm through sand columns to infect weevils. Astatula sand was steam sterilized and the soil moisture was adjusted to 10% by weight. Soil columns were established in PVC tubes. A 15 cm length of tube was fastened to a 5 cm length and the two sections were separated by wire mesh. A single Diaprepes larva was contained in the 5 cm portion at the bottom of the column. Twenty infective juveniles per $cm^2$ soil surface of either nematode species were added to the surface of each column. Each treatment was replicated 15 times. Insect larvae were recovered after 5 days and monitored for two weeks for mortality (FIG. 2a) and recycling rates (FIG. 2b).

Figure 3A:
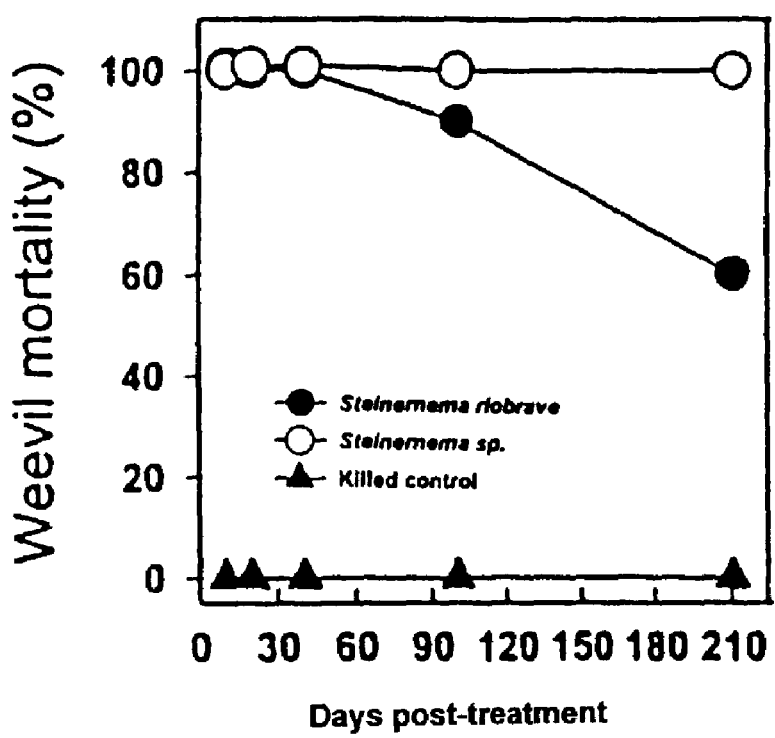
FIG. 3(a) is a graphical comparison of the effect of *S. riobrave* and *S. diaprepesi* citrus root weevil larvae mortality at differing intervals.
Figure 3B:
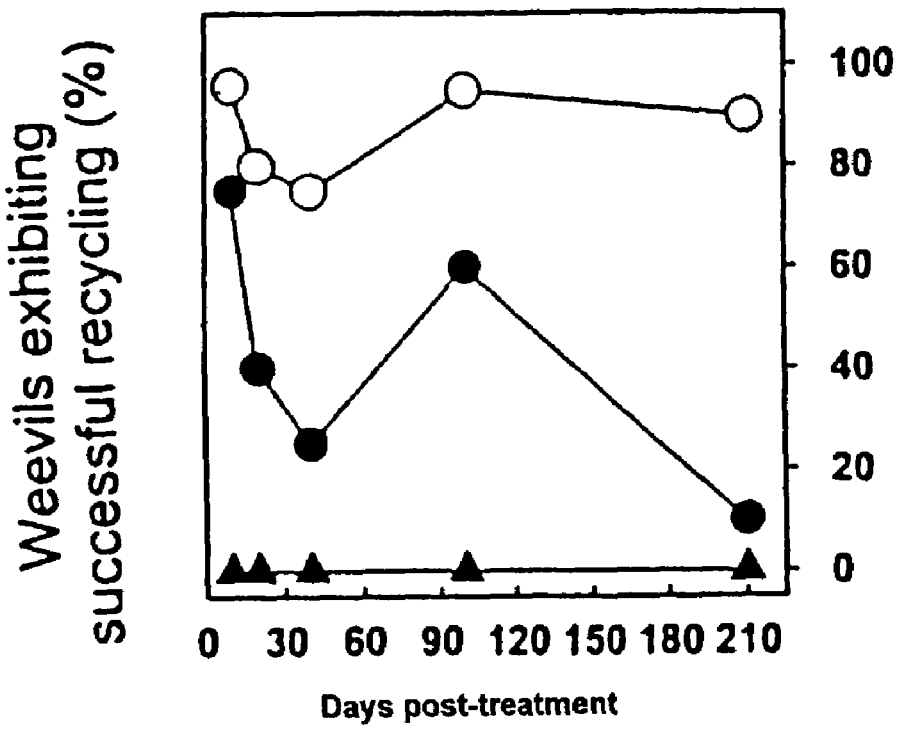
FIG. 3(b) is a graphical depiction of the comparison of *S. riobrave* and *S diaprepesi* recycling rates at differing intervals.

Referring now to FIGS. 3a and 3b, the figures depict persistence of Steinernema riobrave and the newly discovered Steinernema sp. (Steinernema diaprepesi) in the laboratory. A single citrus root weevil larva and 20 nematodes were added to soil in Petri dishes. Ten dishes were maintained for different periods of time, up to 210 days. At each of the various time intervals, a second larva was added to each of 10 dishes. Infection rate and reproduction rate in the second weevil was recorded. Weevil mortality rate is illustrated in FIG. 3a and the percent of seevils recycling is illustrated in FIG. 3b. Decapitated larvae with no added nematodes were used as controls in the experiment.

Following are examples, which illustrate procedures for practicing the invention. These examples should be construed to include obvious variations and not limiting. Unless noted otherwise, all solvent mixture proportions are by volume and all percentages are by weight.

EXAMPLE 1

Nematode Collection and Identification

Nematodes collected from the field were maintained in the laboratory on Galleria mellonella. First and second-generation adult nematodes were obtained by dissecting infected insects after death at 2–4 days and 5–7 days, respectively. Third-stage infective juveniles (IJ) were obtained when they emerged from the cadavers after 7–10 days. Some nematodes were examined alive, others were killed in warm water (at about 40° C.), and still others were fixed in TAF (Courtney et al., 1955) or lactophenol. The specimens were mounted in glycerine. Coverglass supports were used in all cases to avoid flattening specimens. Nematodes of different stages collected from Diaprepes abbreviatus were also used in this study.

Scanning electron microscopy: Adults and IJ were fixed in 3% glutaraldehyde buffered with 0.1 M sodium cacodylate at a pH of about 7.2 for 24 hours at about 8° C. (Nguyen & Smart, 1995). They were post-fixed with 2% osmium tetroxide solution for 12 hours at 25° C., dehydrated in a graded ethanol series, critical point dried with liquid $CO_2$, Mounted on SEM stubs, and coated with gold. Spicules and gubernacula were prepared as suggested by Nguyen and Smart, 1995.

Cross hybridization test: The test was conducted using the first method reported by Nguyen & Smart, 1990, incorporated herein by reference.

DNA Sequencing:

Extraction of DNA: DNA of each nematode species was extracted from a single female (or juvenile) using the method reported by Hominick et al. (1997). The nematode was crushed in 20 μL (10 μL for juvenile) of lysis buffer (50 mM KCl, 10 mM Tris pH=8.3, 2.5 mM $MgCl_2$, 0.45% NP40, 0.45% Tween 20, 0.01% gelatin and 60 μg/mL proteinase K) on a sterilized hanging-drop glass slide and transferred to a sterilized 0.5 mL microcentrifuge tube on ice. The tube was frozen at −80° C. for 10 minutes to completely lyse the cells, incubated at 65° C. for one hour to digest the proteins, followed by a 95° C. incubation for 10 minutes to inactivate proteinase K. The tube was then cooled on ice, and centrifuged at 12,000 rpm for 2 minutes. The supernatant containing the DNA was collected and kept at 4° C. for future use.

PCR amplification: The ITS region of the ribosomal DNA was amplified by the polymerase chain reaction (PCR) in a 100 µL reaction with a DNA polymerase kit from AMRESCO, Inc. All tubes were set up on ice and the following were added to each tube: 10 µL of 10×PCR buffer (100 mM Tris-HCl (pH 8.8), 15 mM MgCl$_2$, 500 mM KCl, 1% Triton X-100), 2 µL of dNTP mixture (10 mM each), 2 µL of 5 pM forward primer, 2 µL of 5 pM reverse primer, 0.5 µL of Thermalase Thr™ (2 U/µL), 74 µL of distilled water, and 10 µL of DNA. To minimize evaporation, 100 µL mineral oil is placed on top of the solution in the tube. The primers used in this study were reported by Hominick et al. (1997):

AB28:

5'-ATATGCTTAAGTTCAGCGGGT-3' (forward) (SEQ ID NO. 1)

and TW81:

5'-GTTTCCGTAGGTGAACCTGC-3' (reverse) (SEQ ID NO. 2).

All PCR reactions were run in a PTC-100 Thermocycler (MJ Research, Inc.) with the cycling profile suggested by Hominick et al. (1997): 1 cycle of 94° C. for 2 min followed by 40 cycles of 94° C. for 30 seconds, 45° C. for 60 seconds, 72° C. for 90 seconds. The last step was 72° C. for 5 minutes.

Sequencing: PCR products were purified with a QIAquick PCR purification kit (QIAGEN Inc., Santa Clarita, Calif.). Purified DNA was sequenced directly using an ABI PRISM™ Dye Terminator Cycling Sequencing Ready Reaction kit (Perkin-Elmer, Corp. Foster City, Calif.). For each reaction the following reagents were added to a 0.5 mL tube: 4 µL Terminator Ready Reaction Mix, 1.5 µL primer (3.2 pM), 2.5 µL DNA from the PCR reaction, 2 µL water and 10 µL of mineral oil to avoid evaporation. The primers used in this step were the AB28 and TW81 described earlier and two internal primers that were synthesized for this study:

KN58=5'-GTATGTTTGGTTGAAGGTC-3' (SEQ ID NO. 3) and

KNRV=5'-CACGCTCATACAACTGCTC-3'(SEQ ID NO. 4).

The KN58 primer was designed with the Prime program from the Genetic Computer Group (GCG) Package; the KNRV primer was selected from the alignment of 4 sequences obtained by sequencing PCR products of 4 species with the two AB28 and TW81 primers. These two internal primers were used to completely sequence both strands of the PCR product. The sequencing reactions were done in a PTC-100 thermal cycler, and the following cycling profile was used: 25 cycles of 96° C. for 30 seconds, 50° C. for 15 seconds, and 60° C. for 4 minutes. The sequencing product was ethanol precipitated to remove primers and unincorporated nucleotides. For this, 1 µL 3 M sodium acetate, pH 4.6 and 25 µL 95% ethanol were added to the 10 µL sequencing reaction, incubated on ice for 10 minuntes and centrifuged in a microcentrifuge for 15 minutes. The pellet was washed with 70% ethanol and dried in a vacuum desiccator. The DNA was sequenced at the DNA Sequencing Core Laboratory of the University of Florida's Interdisciplinary Center on an Applied Biosystems Model 373A DNA Sequencer or 377 DNA Sequencer. The sequences flanked by the AB28 and TW81 primers were assembled using Auto-Assembler Version 2 (Perkin-Elmer). At least two sequencing reactions were performed per strand.

Multiple alignment, ratios of similarity, and composition were obtained using GCG pileup, old distances, and composition programs.

Molecular Taxonomy

Referring now to FIGS. 1(a) through (e), homology among the sequences of the 4 species, S. feltiae (SEQ ID NO: 5), S. oregonense (SEQ ID NO: 6), S. glaseri (SEQ ID NO: 7), and S. diaprepesi n. sp. (SEQ ID NO: 8) is shown. Sequence length, composition percentage is illustrated in Table 4. Similarity ratios are illustrated in Table 5. The comparison of the indicia indicate that they are different species.

TABLE 4

Sequence lengths of ITS region, and composition of 4 species of Steinemema

| Species (Seq length) | ITS1 (bp) | 5.8S (bp) | ITS2 (bp) | A (%) | C (%) | G (%) | T (%) |
|---|---|---|---|---|---|---|---|
| S. diaprepesi (808 bp) | 301 | 158 | 313 | 24.1 | 20.6 | 24.1 | 31.2 |
| S. feltiae (766 bp) | 275 | 157 | 298 | 25.5 | 16.7 | 21.5 | 36.3 |
| S. glaseri (774 bp) | 279 | 157 | 302 | 22.5 | 21.2 | 26.7 | 29.6 |
| S. oregonense (759 bp) | 267 | 157 | 297 | 24.9 | 18.1 | 22.1 | 34.9 |

TABLE 5

Pairwise similarity among 4 species of Steinernema*

| Species | S. feltiae | S. oregonense | S. glaseri | S. diaprepesi |
|---|---|---|---|---|
| S. feltiae | 1.0000 | 0.8972 | 0.6097 | 0.6332 |
| S. oregonense |  | 1.0000 | 0.6008 | 0.6271 |
| S. glaseri |  |  | 1.0000 | 0.7429 |
| S. diaprepesi |  |  |  | 1.0000 |

*expressed as the number of matches between each sequence pair divided by sequence length

EXAMPLE 2

Nematode Persistence and Natural Control by Nematodes

The nematode described herein is effective for controlling a variety of insects. Without being limited thereto, pests of particular interest known to be susceptible to treatment are agronomically important insects. This is especially true for the citrus root weevil, and in particular Diaprepes abbreviatus. The nematode may be applied to control these agronomically important insects on a number of crops, non-exclusively including citrus.

Production of the nematode may be accomplished using in vivo or in vitro techniques known in the art. As described in the Examples herein, Steinernema diaprepesi may be initially recovered from soil samples taken from citrus groves in Polk County, Fla. Following isolation from the environment, the nematodes may then be reared in vivo in susceptible host insects such as Diaprepes abbreviatus or Galleria mellonella, as illustrated in the Examples. In accordance with a preferred embodiment, the nematodes may also be produced on a large scale using in vitro rearing techniques well known in the art. See, for example, Friedman et al., Mass Production in Liquid Culture of Insect-Killing Nematodes, U.S. Pat. No. 5,023,183 (issued Jun. 11, 1991), incorporated herein by reference. Other methods are taught in U.S. Pat. Nos. 6,033,658; 5,694,883; and 5,554,533; also incorporated herein by reference. In accordance with any known technique, the nematodes may be subsequently harvested and collected in pure or substantially pure form.

When entomopathogenic nematodes are applied to soil in Florida, their population density declines rapidly. Irrigation during and following nematode application increases the survival and efficacy of nematodes (Downing, 1994); however, large numbers of nematodes can remain near the soil surface and die (Duncan & McCoy, 1996). Although recycling of exotic nematodes has been detected in experimental plots in the field, the level of long-term insect management does not appear to be significant. In a greenhouse experiment in which *S. riobrave* were applied at various intervals to potted citrus seedlings that were infected repeatedly with neonate larvae of *D. abbreviatus*, fibrous root weights of trees increased directly with the number of nematode applications (Duncan & McCoy, unpublished). Compared to trees not infested by weevils, fibrous roots of infested trees were reduced significantly even when treated monthly with nematodes. These data suggest that very limited feeding by the insect is likely to reduce fruit yield by diverting carbohydrates to fibrous root growth, and that low persistence by the nematode requires frequent application to mitigate the problem.

Suitable formulations for commercial insecticidal applications can be prepared from nematodes isolated from the environment, particularly in vitro cultivated populations of the nematodes, or pure or substantially pure nematodes. Because of the moisture required by nematodes for continued viability and infectivity, the nematodes are advantageously applied in combination with a suitable inert carrier or vehicle as is known in the art. Such a carrier is optionally substantially biologically pure. The formulations described herein are storage stable and nematode viability can be maintained for up to one month with refrigeration.

As a practical matter, to facilitate handling and transport of the biopesticide, and to prevent dessication, the formulations of the nematode and carrier should be enclosed within a container such as a drum, jug, flask or plastic bag as is known in the art.

Of particular interest are formulations employing water as a carrier, with a population of the nematodes suspended therein. In an alternative embodiment the carrier may be a solid phase material or encapsulating agent, upon or within which the nematodes can be immobilized. Suitable carriers of this type include but are not limited to hydrogel agents such as alginate gels (U.S. Pat. Nos. 4,753,799; 4,701,326 and 4,615,883 to Nelsen); wheat-gluten matrices (U.S. patent application Ser. No. 07/560,792, filed Jul. 30, 1990, to Connick and Nickle); starch matrices (U.S. Pat. No. 4,859,377 to Shash et al.); wheat-bran bait pellets (U.S. Pat. Nos. 6,110,480; 5,965,149; and 5,807,566; as well as in Capinera and Hibbard [J. Agric. Entomol., 4:337–344, (1987)]; clay particles; polyacrylamide gels; or synthetic polymers as are known in the art. Preferred alternative carriers and methods for immobilizing nematodes are described.

Formulations of alginate gels containing the nematodes provide the added benefit of enhanced viability after storage, while allowing subsequent conversion to an aqueous liquid by dissolution of the alginate with sodium citrate. When the carrier is other than water, sufficient moisture should be provided to ensure viability and infectivity of the nematodes.

Besides the active agent itself, other additives and adjuncts may be formulated into the compositions of the invention. Examples of these include nutrients, humectants, feeding stimulants (phagostimulants), UV protectants, inert fillers, and dispersants. Humectant materials include but are not limited to glycerol, sugars such as sucrose, invert emulsions, and cellulose ethers.

In use, an insecticidally effective amount of the nematode of this invention is applied to the locus of, or in the vicinity of, the insects to be controlled. The actual effective amount may be readily determined by the practitioner skilled in the art, and may vary with the species of pest, stage of larval development, the type of vehicle or carrier, the period of treatment, environmental conditions (especially moisture and soil texture), and other related factors.

EXAMPLE 3

Application Timing and Frequency

Recommendations about when and how often to apply entomopathogenic nematodes have been inferred from seasonality of emergence of adult insects from the soil, from estimates of nematode persistence following application from research on physical causes of nematode mortality, and by considering the cost of applying nematodes.

Time of day is also important when scheduling applications. Nematodes applied beneath the canopy of a tree survive in direct proportion to their proximity to the tree trunk where evaporation of soil moisture and exposure to ultraviolet radiation are least (Duncan et al., 1996) Molyneaux & Bedding, 1984; Faugler & Boush, 1978). Application of nematodes in the evening provides the longest possible time for their establishment before being exposed to desiccation and sunlight.

Because nematodes attack insects in the soil and show little evidence of significant persistence, nematodes will have the greatest effect if applied when numbers of insects in soil are highest. Emergence from soil of *D. abbreviatus* and another species of root weevil, *Pachnaeous litus*, is seasonal in Florida, with maximum emergence in late spring. Adult census data suggest that the rate of egg deposition in the tree canopy increases in early summer. Thus, by autumn the surviving larvae in the soil have likely reached a maximum density, because low winter temperatures greatly reduce ovipositional activity. As temperatures increase in the spring, larval and pupal development continues until adults emerge from the soil. Because larval development requires a minimum of 4 months, it is likely that most larvae, which enter soil during mid-to-late summer, emerge the following spring.

Growers generally do not apply more than two applications of nematodes per year for economic rather than empirical reasons. Based on the pattern of adult emergence from soil, there is general consensus that an application of nematodes in the autumn presents the parasites with their greatest opportunity to locate insect prey. A second application of nematodes in spring when soil temperatures are high enough for nematode activity, but before adult emergence occurs, is practiced by many growers and researchers (See Bullock et al., 1999). To reduce the deposition of larvae into the soil following a springtime nematode treatment, management of above ground stages of the insect is recommended at peak adult emergence. It has also been suggested that an application of nematodes in summer, when rainfall and soil temperatures are highest, provides the worms with ideal conditions for parasitism at a time when natural control is highest (Knapp, 1998).

EXAMPLE 4

Application Methods

Entomopathogenic nematodes are applied to citrus either with herbicide application equipment or via under-tree, low-volume irrigation systems. The latter method has the advantages of eliminating the cost of driving equipment through the orchard and of depositing nematodes only in irrigated soil. However, the spatial pattern of nematode deposition throughout a grove is less consistent when applied by irrigation lines, particularly when the flow rate is low, as in drip-irrigation systems (Conner et al., 1998). Micro-sprinkler irrigation systems have higher flow rates and deliver nematodes more uniformly. Numbers of nematodes delivered to tree rows is reasonably uniform with distance from the injection point. A similar pattern is seen within the tree rows, except that trees at the very ends of rows receive significantly fewer nematodes, due to changes in water flow as water reaches the ends of lines.

Various common-sense factors should be considered with regard to application equipment. Holding/mixing tanks should be thoroughly cleaned of nematode-detrimental chemical residues from previous operations. Nematodes should not be combined with other chemicals to be applied to trees. The pH of delivery water should not be excessively low or high. Artesian well water generally lacks sufficient oxygen for nematodes and should not be used. Pumps that generate excessive heat should not be used for injecting nematodes into irrigation systems or for maintaining nematodes suspended in holding tanks, as the heat may destroy or inhibit the Nematode.

Label rates for commercial preparations of *S. riobrave* and *H. indica* in citrus are 200 million and 100 million nematodes per acre, respectively. The label rate for *S. diaprepesi* is generally between 100 million and 200 million nematodes per acre. However, the actual rate of application varies with tree age, because the under-canopy surface area of young trees is an order of magnitude less than that of mature trees. Thus, preferred application rates may vary from more than 200 to fewer than 20 nematodes per $cm^2$ soil surface.

Without being limited thereto, in accordance with the preferred embodiment, the nematodes are applied at a concentration greater than or equal to about $2.5 \times 10^4$ infective juveniles per $m^2$ soil or field, and especially at a concentration greater than or equal to about $1 \times 10^5$ or $2 \times 10^5$ infective juveniles per $m^2$ of soil or field. Surprisingly, these inoculum levels are six times less than the levels of other entomopathogenic nematodes used to control other soil insect pests. See Miller and Bedding, Entomophaga, 27:109–114, (1982). In the alternative, the concentration of nematodes to be applied may also be determined relative to the density of the target insects, if known. The nematodes are preferably applied at a concentration greater than or equal to about 10 infective juvenile nematodes per target insect, and especially at a concentration greater than or equal to about 100 infective juvenile nematodes per target insect.

Because of the moisture requirements of these nematodes, and since the soil is their natural habitat and the citrus root weevil larvae drop to the ground to pupate as part of their life-cycle, techniques wherein the nematodes are applied to the soil are desirable. In accordance with a particularly preferred embodiment for use in areas employing irrigation, the nematodes may be admixed with irrigation water prior to or at the time of irrigation, effectively distributing the nematodes across the field. In order to maximize insect kill, the application of the nematodes to the soil should be timed to the development of prepupae, ensuring the highest rate of parasitism by the nematodes. Because *Steinernema diaprepesi* actively seek, penetrate, and parasitize the target insect pupae and prepupae, feeding by the insect upon the formulation of the nematode is not required. Further, this nematode has the capability of remaining viable and maintaining its infectivity in sandy soil for extended periods after application, providing the added advantage of residual insecticidal activity.

Another technique for soil application employs encapsulated or pelletized formulations of the nematode. The capsules or pellets containing the nematode may be applied to the soil prior to emergence of the crop. In crops such as corn or the like, the application can occur just prior to larval exit from the corn ear, such as by spreading or spraying. Depending upon the carrier selected, the nematodes may be released from the capsules or pellets as they degrade in the soil (Connick and Nickle) or upon ingestion by the insect. While soil application techniques are preferred, the formulations of the nematode may also be applied directly upon the crop such as by spraying.

Inasmuch as the preceding disclosure presents the best mode devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

REFERENCES

Courtney, W. D., D. Polley, and V. I. Miller (1955) ATAF, an improved fixative in nematode technique@ *Plant Disease Reporter* 39:570–571.

Hominick, W. M., B. R. Briscoe, F. G. del Pino, Jian Heng, D. J. Hunt, E. Kozodoy, Z. Mracek, K. B. Nguyen, A. P. Reid, S. Spiridonov, D. Sturhan, C. Waturu, and M. Yoshida (1997) ABiosystematics of entomopathogenic nematodes: current status, protocols and definitions@ *Journal of Helminthology* 71:271–298.

Nguyen, K. B., and G. C. Smart, Jr. (1990) *A. Steinernema scapterisci* n. sp. (Rhabditida: Steinernematidae)@ *Journal of Nematology* 22:187–199.

Nguyen, K. B., and G. C. Smart, Jr. (1995) A Scanning electron microscope studies of *Steinernema glaseri* (Nematoda: Steinernematidae)@ *Nematologica* 41:183–190.

We claim:

1. A method of protecting or treating plants or fruit from insect infestations comprising applying an effective amount of a composition comprising *Steinernema diaprepesi* to plants or fruit in need thereof to protect said plants or fruit from said insect infestation.

2. The method of claim 1 wherein said composition is applied to the soil around the roots of the plant.

3. The method of claim 1 wherein said composition is applied to the roots.

4. The method of claim 1 wherein said composition is applied to said plants or fruit by low pressure spraying.

5. The method of claim 1 wherein said composition is applied by low pressure, low volume irrigation.

6. The method of claim 1 wherein said composition is contained in a biodegradable capsule or pellet for application.

7. The method of claim 1 wherein said composition has a concentration of *Steinernema diaprepesi* of about $2.5\times10^4$, or greater, infective juveniles per $M^2$ of soil.

8. The method of claim 1 wherein said composition is applied at a concentration of about 10 infective juveniles per target insect.

9. The method of claim 1 wherein said insect is a curculionid insect.

10. The method of claim 9 wherein said curculionid insect is *Diaprepes abbreviatus*.

11. The method of claim 1 wherein said composition further comprises at least one additive selected from the group consisting of a carrier, nutrient, humectant, feeding stimulant, UV protectant, dispersant, and an inert filler.

12. The method of claim 11 wherein said carrier is selected from the group consisting of water, alginate gel, wheat gluten matrix, starch matrix, wheat-bran bait pellets, clay particles, and polyacrylamide gel.

13. The method of claim 11 wherein said humectant is selected from the group consisting of glycerol, sucrose, fructose, lactose, maltose, glucose, mannose, inert emulsions, and cellulose ether.

* * * * *

UNITED STATES PATENT AND TRADEMARK OFFICE
CERTIFICATE OF CORRECTION

PATENT NO. : 7,014,859 B1  
APPLICATION NO. : 10/197993  
DATED : July 18, 2002  
INVENTOR(S) : Larry W. Duncan and Khuong B. Nguyen Page 1 of 1

It is certified that error appears in the above-identified patent and that said Letters Patent is hereby corrected as shown below:

Title, page, item [57],

Abstract, line 12
"89.6 78-114)." should read --89.6 (78-114).--.

Column 1,
Line 59, "Steinemematidae" should read -- Steinernematidae --.

Column 4,
Line 66, "=89.6 78-114)." should read --=89.6 (78-114).--.

Column 9,
Line 53, "seevils" should read -- weevils--.

Column 16,
Line 42, "ABiosystematics" should read -- A Biosystematics --.

Signed and Sealed this

Twenty-second Day of August, 2006

JON W. DUDAS  
*Director of the United States Patent and Trademark Office*

UNITED STATES PATENT AND TRADEMARK OFFICE
CERTIFICATE OF CORRECTION

PATENT NO. : 7,014,859 B1  Page 1 of 1
APPLICATION NO. : 10/197993
DATED : March 21, 2006
INVENTOR(S) : Larry W. Duncan and Khuong B. Nguyen It is certified that error appears in the above-identified patent and that said Letters Patent is hereby corrected as shown below:

Title, page, item [57],

Abstract, line 12
"89.6 78-114)." should read --89.6 (78-114).--.

Column 1,
Line 59, "Steinemematidae" should read -- Steinernematidae --.

Column 4,
Line 66, "=89.6 78-114)." should read --=89.6 (78-114).--.

Column 9,
Line 53, "seevils" should read -- weevils--.

Column 16,
Line 42, "ABiosystematics" should read -- A Biosystematics --.

This certificate supersedes Certificate of Correction issued August 22, 2006.

Signed and Sealed this

Tenth Day of October, 2006

JON W. DUDAS
*Director of the United States Patent and Trademark Office*